United States Patent [19]

Laso

[11] 4,296,102

[45] Oct. 20, 1981

[54] METHOD OF COMBATING AMEBIASIS IN HUMANS

[76] Inventor: Felipe Laso, Montecito 59, Mexico City, Mexico

[21] Appl. No.: 158,649

[22] Filed: Jun. 12, 1980

[51] Int. Cl.$^3$ .................... A61K 33/40; A61K 33/22; A61K 33/20

[52] U.S. Cl. .................... 424/130; 424/148; 424/149

[58] Field of Search .................... 424/148, 149, 130

[56] References Cited

U.S. PATENT DOCUMENTS 2,701,781  2/1955  de Guevara .................... 424/148

3,147,124  9/1964  Wentworth .................... 424/149 X

OTHER PUBLICATIONS

Merck Index, 9th Ed. (1976), Nos. 4691, 8416 and 7438.

*Primary Examiner*—Frank Cacciapaglia, Jr.
*Attorney, Agent, or Firm*—Miller, Welsh & Kratz Parmelee

[57] ABSTRACT

A method for combating amebiasis in humans comprising orally administering to said humans an effective amount of a perborate-stabilized aqueous solution of chlorine oxides, said solution containing about 4–12% by weight of sodium or potassium perborate and a peroxide or percarbonate.

4 Claims, No Drawings

METHOD OF COMBATING AMEBIASIS IN HUMANS

BACKGROUND OF THE INVENTION

1. Field of the Invention

The present invention is directed to a method for combating amebiasis in humans. As is known, amebiasis is due to attack by pathogenic protozoa and is a widespread affliction, especially in countries such as tropical countries or those having unsanitary areas. Although some compounds are known for treatment of amebiasis, generally such known compounds have undesirable side effects. Also treatment with such compounds is often expensive. A need exists for an inexpensive method for combating amebiasis in either living or cyst condition and the present invention is directed to such a method where a perborate-stabilized aqueous solution of chlorine oxides is orally administered to afflicted persons to combat the affliction.

2. Prior Art

The stabilization of aqueous solutions of chlorine dioxide by the use of perborates has been disclosed in U.S. Pat. No. 2,701,781 the contents of said patent being incorporated by reference herein. As disclosed in said patent, a stabilized solution of chlorine dioxide in water can be formed by the combination of an inorganic boron compound, such as sodium tetraborate, boric acid or sodium perborate, and chlorine dioxide in the presence of an excess of water. The stabilized composition so formed is described therein as an antiseptic that has no irritative tendency. Urea is suggested as an additive to the composition where the same is to be used as an oral antiseptic.

Additional uses for such stabilized aqueous chlorine dioxide compositions have been disclosed, for example, in U.S. Pat. No. 3,147,124, where a stabilized aqueous chlorine dioxide solution is described as a useful germicide upon addition of the same in a cheese making process.

It has now been found that perborate-stabilized aqueous solutions of chlorine oxides are useful in treating amebiasis in humans.

SUMMARY OF THE INVENTION

A method for combating amebiasis in humans comprises orally administering to a human affected therewith an effective amount of a perborate-stabilized aqueous solution of chlorine oxides. The perborate-stabilized aqueous solution of chlorine oxides, such as chlorine dioxide, containing 4-12 parts by weight of sodium or potassium perborate per liter of water is orally administered to the human in an amount of between 5-20 drops (0.25 cc to 1.0 cc) three times per day for a period of at least fifteen days, preferably about 21 days. The perborate-stabilized aqueous solution of chlorine oxides also preferably contains a peroxide such as hydrogen peroxide, sodium peroxide or potassium peroxide, or a percarbonate such as sodium percarbonate or potassium percarbonate.

DETAILED DESCRIPTION

As described in U.S. Pat. No. 2,701,781, a perborate stabilized aqueous solution of chlorine dioxide can be produced in which the chlorine dioxide is apparently held in the form of a labile complex with the boron compound. Such perborate-stabilized chlorine oxide solutions have now been found to combat amebiasis in humans through oral administration thereof.

The perborate stabilized aqueous solutions usable in the present method are formed by preparing an aqueous solution containing 4 to 12 parts by weight of sodium or potassium perborate per liter of water, the solution prepared by adding chlorine dioxide as a gas or formed in situ in the aqueous media by addition of chlorite and/or hypochlorite salts under acidic conditions, i.e., at a pH of less than 7.0, preferably a pH of between 2.5-4.5. While chlorine dioxide is believed to be the oxide of chlorine present in the solution, other oxides of chlorine may be present. During the passage or formation of chlorine dioxide in the aqueous solution, under acidic conditions, it is believed that chlorous and chloric acids are formed which react with the perborates and gradually forms a clear, transparent aqueous solution.

In addition to the sodium or potassium perborate, the aqueous solution preferably has added thereto a peroxide selected from hydrogen peroxide, sodium peroxide or potassium peroxide, or a percarbonate such as sodium percarbonate or potassium percarbonate. The amount of peroxide or percarbonate added should be between .1 to 20 parts per liter of water, preferably between about 8-15 parts per liter of water.

In order to enhance the palatability of the aqueous stabilized solution of chlorine oxides, urea is added in an amount of between 0.5 to 20 parts per liter of water, with about 6-20 parts preferred.

In the formation of a preferred aqueous solutions of perborate stabilized chlorine oxide solutions usable in the present method, there would be added to 1 liter (1,000 cc's) of water the following:

80-120 grams sodium chlorite
90-130 grams sodium hypochlorite (13%)
5-7.5 c.c. of 37.7% hydrochloric acid
2-4.5 c.c. of 98.15% sulfuric acid
4-12 grams sodium or potassium perborate
8-15 grams sodium peroxide or an equivalent amount of potassium peroxide, hydrogen peroxide potassium percarbonate, or sodium percarbonate
6-20 grams urea.

The resultant solution (about 1100-1120 cc's) has a density of between about 1.08 to 1.10.

As an example of a specific aqueous solution of perborate-stabilized chlorine oxides produced according to the present inventions, there was added to 1 liter (1000 cc's) of water the following:

90 grams sodium chlorite
105 grams sodium hypochlorite (13%)
5.9 cc's of 37.7% hydrochloric acid
3.05 cc's of 98.15% sulfuric acid
5 grams sodium perborate
10 grams sodium peroxide
10 grams urea The resultant solution (1150 cc's) had a density of 1.09.

The perborate stabilized aqueous solution of chlorine oxides formed, as above, was found to combat amebiasis in humans by oral administration of the solution.

The amount of perborate-stabilized aqueous solution of chlorine oxides to be orally administered is generally between about 5-20 drops of the solution (density of 1.09), two to three times a day, a total of between 15-60 drops, carried out for a period of at least about fifteen days, preferably for 21 days or more. Specific amounts would depend upon the size of the recipient. For example, a relatively small person of about 150 pounds of less would be give 10 drops of the solution, three times a day, for fifteen days; an average size person of between 150-200 pounds weight would be given 15 drops of the solution, three times a day, for fifteen days; while a larger person, in excess of about 200 pounds weight would be given 20 drops of the solution, three times the first day and then 15 drops of the solution, three times, a day, for the next succeeding fourteen days.

As an example of the effectiveness of the present method, a male, age 20 years, was treated for amebiasis by oral administration of a perborate-stabilized aqueous solution of chlorine oxides (density of 1.09) in an amount of 5 drops of solution, three times per day. After twenty-two days of treatment, the subject was found to be in very good condition and no further treatment for amebiasis was required.

As a further example of the efficacy of the present method, a female, age 31 years, was treated for amebiasis by oral administration of a perborate-stabilized aqueous solution of chlorine oxides (density of 1.09) in an amount of 8 drops of solution, two times per day. After sixteen days of treatment, the subject was found to be in very good condition and no further treatment for amebiasis was required.

Oral administration of the perborate-stabilized aqueous solution of chlorine oxides according to the present invention is preferably carried out by mixing the requisite solution with water, tea, or milk which the human then drinks.

I claim:

1. The method of combating amebiasis in a human suffering from amebiasis, comprising orally administering to said human, an amount effective to combat said amebiasis, of a perborate stabilized aqueous solution of chlorine oxides formed by adding to 1000 cc of water the following:
   80-120 grams sodium chlorite
   90-130 grams sodium hypochlorite (13% aqueous solution)
   5-7.5 cc of 37.7% hydrochloric acid
   2-4.5 cc of 98.15% sulfuric acid
   4-12 grams of an inorganic perborate selected from the group consisting of sodium perborate and potassium perborate, and
   8-15 grams of sodium peroxide or an equivalent amount of potassium peroxide, hydrogen peroxide, potassium percarbonate, or sodium percarbonate.

2. The method of claim 1 wherein said perborate stabilized aqueous solution is formed by adding to 1000 cc of water the following:
   90 grams sodium chlorite
   105 grams sodium hypochlorite (13%)
   5.9 cc's of 37.7% hydrochloric acid
   3.05 cc's of 98.15% sulfuric acid
   5 grams sodium perborate
   10 grams sodium peroxide
   10 grams urea; and the resultant solution has a density of about 1.09.

3. The method of claim 1 wherein said aqueous solution is orally administered to said human two to three times per day for a period of at least fifteen days.

4. The method of claim 3 wherein said aqueous solution is administered in an amount of between 5 to 20 drops to said human, three times per day, for said period.

* * * * *